United States Patent
Silberer

(12) 
(10) Patent No.: US 6,589,284 B1
(45) Date of Patent: Jul. 8, 2003

(54) MODULAR SOCKET FOR A BALL JOINT PROSTHESIS

(75) Inventor: Paul Silberer, Waghausel (DE)

(73) Assignee: CeramTec AG, Plochingen (DE)

( * ) Notice: Subject to any disclaimer, the term of this patent is extended or adjusted under 35 U.S.C. 154(b) by 0 days.

(21) Appl. No.: 10/009,954

(22) PCT Filed: Jun. 13, 2000

(86) PCT No.: PCT/EP00/05427

§ 371 (c)(1), (2), (4) Date: Feb. 28, 2002

(87) PCT Pub. No.: WO00/76427

PCT Pub. Date: Dec. 21, 2000

(30) Foreign Application Priority Data

Jun. 14, 1999 (DE) .......................... 199 26 923

(51) Int. Cl.⁷ ............................ A61B 17/58; A61F 2/32
(52) U.S. Cl. ...................... 623/22.29; 606/91; 606/99
(58) Field of Search ........................ 623/22.29, 22.28, 623/212.24, 22.21, 22.2, 22.12, 18.11, 16.11, 22.23; 606/81, 91, 99

(56) References Cited

U.S. PATENT DOCUMENTS

| | | | |
|---|---|---|---|
| 4,813,961 A | * 3/1989 | Sostegni | 623/23.39 |
| 5,092,897 A | 3/1992 | Forte | |
| 5,147,407 A | * 9/1992 | Tager | 623/22.27 |
| 5,480,448 A | * 1/1996 | Mikhail | 623/22.24 |
| 5,507,826 A | * 4/1996 | Besselink et al. | 623/22.29 |
| 5,658,338 A | 8/1997 | Tullos | |
| 5,725,591 A | 3/1998 | Decarlo, Jr. | |
| 5,766,260 A | 6/1998 | Whiteside | |
| 5,904,688 A | * 5/1999 | Gilbert et al. | |
| 5,935,175 A | * 8/1999 | Ostiguy et al. | 623/22.28 |
| 6,022,357 A | * 2/2000 | Reu et al. | 606/99 |
| 6,027,505 A | * 2/2000 | Peter et al. | 606/91 |
| 6,042,611 A | * 3/2000 | Noiles | 623/22.21 |
| 6,063,123 A | * 5/2000 | Burrows et al. | 623/22.21 |
| 6,063,124 A | * 5/2000 | Amstutz | 623/22.21 |
| 6,132,469 A | * 10/2000 | Schroeder | 623/22.24 |
| 6,162,257 A | * 12/2000 | Gustilo et al. | 623/23.32 |
| 6,468,281 B1 | * 10/2002 | Badorf et al. | 606/91 |
| 6,475,243 B1 | * 11/2002 | Sheldon et al. | 623/22.28 |
| 6,488,713 B1 | * 12/2002 | Hershberger | 623/22.11 |

FOREIGN PATENT DOCUMENTS

| | | |
|---|---|---|
| DE | 44 02 675 | 6/1957 |
| DE | 43 35 931 | 4/1995 |
| DE | 196 11 249 | 9/1997 |
| DE | 197 08 604 | 10/1998 |
| EP | 0 091 315 | 10/1983 |
| EP | 0 142 759 | 5/1985 |
| EP | 0 551 794 | 7/1993 |
| EP | 0 694 294 | 1/1996 |
| EP | 0 811 360 | 12/1997 |
| EP | 0 853 928 | 7/1998 |

* cited by examiner

*Primary Examiner*—Pedro Philogene
*Assistant Examiner*—D. Austin Bonderer
(74) *Attorney, Agent, or Firm*—Fulbright & Jaworski L.L.P.

(57) ABSTRACT

Conventional modular sockets for ball joint prostheses usually consist of a metal socket housing and a skid-type shell inserted in the housing. Ceramic skid-type shells are usually press-fitted in the socket housing. The socket housing may become stiff, thereby causing a migration of the generic sockets. If the skid-type shell is inserted improperly, material may chip off at the edge of the skid-type shell. Due to the various designs of sockets, skid-type shells with different outer diameter have to be made available for every gliding surface diameter. The invention provides for a ceramic skid-type shell (2) that is rigidly inserted into a biocompatible metal ring (5). Said ring (5) is provided with at least three radially outwards extending fixing elements (6). Said fixing elements (6) engage with respective recesses (8) in the socket housing (7). The ring (5) is spaced apart from the socket housing (7) by a gap (14).

11 Claims, 3 Drawing Sheets

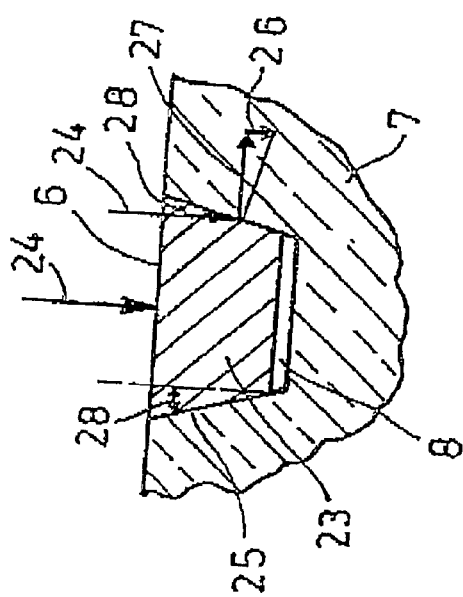
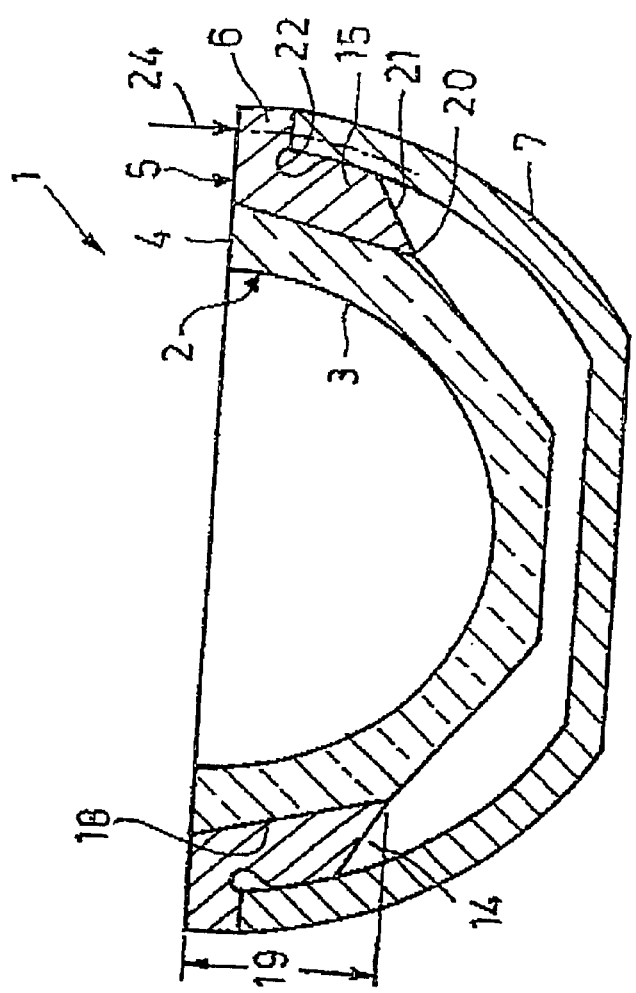

MODULAR SOCKET FOR A BALL JOINT PROSTHESIS

The invention concerns a modularly constructed socket for a ball-joint prosthesis for insertion in bone tissue.

Modularly constructed sockets for ball-joint prostheses usually consist of an outer metal shell, to be inserted in the bone tissue, as the socket shell, and an inner sliding cup placed in the socket shell. This sliding cup can consist of ceramic material, for example, and be fixed to the metal shell, the socket shell, with a conical clamp. Such a socket is described for example in DE 43 35 931 A1. In DE 44 02 875 A1 a socket shell is described in which the inner sliding cup is placed in the socket shell without a conical clamp. So that the sliding cup is protected from rotating or becoming detached, yet can be removed from its seat and exchanged without damage, it is secured by a holding ring in the metal cup, which is screwed to the anterior face of the socket shell.

With the known forms of construction, the outer edge of the metal cup for emplacement in the bone tissue, the edge of the socket shell, is reinforced. The socket shell loses its elasticity. As a result, increased migration of the socket shell in the bone can occur. This leads to gradual loosening of the implant in the bone.

A further problem is matching the sliding cup to the dimensions of the socket shell. The measurements of the socket, essentially the diameter of the ball and consequent internal diameter of the sliding cup, are essentially determined by the age of the patient and his/her bodily stature. With conical clamping fitting in particular, the outer contours of the sliding cup must conform very exactly to the inner contours of the socket shell. Upon any subsequent surgical operation, it is therefore advantageous if there can be retention of at least the shaft in the thigh and the socket shell in the pelvic girdle by the endoprosthesis and only the ball of the ball-joint prosthesis and the sliding cup need to be replaced.

The object of the present invention consists of improving the emplacement of the ceramic sliding cup in a metal socket shell and to facilitate the removal of the sliding cup from the socket shell during any repeat surgery.

This object is achieved with the help of the characteristic features of claim 1. Advantageous refinements of the invention are claimed in the sub claims, to which belongs a piece of apparatus that is advantageously appropriate for manipulation of a sliding cup.

The modularly constructed socket for a ball-joint prosthesis according to the invention differs from the prostheses currently available in that the ceramic cup is not placed directly in the socket shell. The ceramic cup is inserted securely in a ring of biocompatible metal and this ring is placed in the socket shell. For securing the ring to the sliding shell, at least three securing elements protruding radially outwardly, are provided on the ring. These securing elements fit into a recess in the socket shell. The ring does not lie directly on the socket shell, but is separated from it by a gap. As a result of the securing of the cup according to the invention, reinforcing of the socket shell is impeded by the sliding cup, as occurs with currently available conical surface clamping of the sliding cup and socket shell. A possible migration of the socket shell as a result of the reinforcing is accordingly avoided. The socket shell retains its elasticity. Furthermore, it prevents bad or careless positioning of the sliding cup in the socket shell giving rise to flaking of the cup rim, thus making it unusable. The surgeon's work is made easier, as positioning of the sliding cup in the socket shell under operating conditions is made easier.

The connection between the sliding cup and the ring can be achieved either with conical clamping or shrinking on of the ring. With shrinking on, the ring is warmed and pulled over the sliding cup. On cooling, a shrink connection exists.

To achieve efficient positioning of the sliding cup in the socket shell and at the same time efficient balance within the shell, it is an advantage if the gap between sliding cup and socket shell has the same measurements everywhere. To produce and ensure a constant distance between sliding cup and socket shell, the securing elements have spacers. The spacers can also be constructed so that, by support on the wall of the shell in the region of the securing elements, an equal distribution of the load in the socket shell is ensured. Depending on the size of the socket shell and the sliding cup, the spaces between the sliding cup and socket shell are between about 1 mm and 1.8 mm.

To ensure anchoring of the ring with the sliding cup in the socket shell, the securing elements widen in the radial direction in a wedge shape and the recesses in the socket shell which the securing elements fit match the contours of the securing elements. When a load is placed on the sliding cup, this will seek to push out the socket shell. The wedge shape ensures that this pressing of one out of the other is prevented and the securing elements of the sliding cup ensure that the shell retains its shape as a result of its clamping action, so that dislocation of the sliding cup from the socket shell due to expansion of the latter is avoided.

The load distribution in the socket shell by the securing elements in the socket is further improved if the securing elements narrow in a wedge-shaped fashion in the direction of emplacement in the socket shell and the recesses in the socket shell are matched to the contours of the securing elements. As a result of the shaping of the recesses, a one-sided load distribution via the securing elements in the direction of the meridian is available in the socket shell which has generally the shape of a hemisphere or a section of a sphere. As a result of the wedge-shaped narrowing of the securing elements, not only are load components in the direction of the meridian in the spherical surface but also vertically in the direction of the circumference of the socket shell so that an equilibrium of the load distribution in the region of the recess in the shell is assured.

Because of the various forms of shell, there are various internal diameters for uptake of the cups, which have one and the same internal diameter, as they must fit one and the same ball-joint size. Therefore there is a further advantage to embedding the sliding cups in rings, in that the external diameter of the cup no longer has to conform to various forms of the socket shells. It is sufficient to produce a sliding cup with the predetermined external diameter and fit it to the shell by means of rings of varying thickness. The invention is therefore based on the concept that it is easier to produce a ceramic sliding cup in a single size, because in that way the behaviour of several shapes and the corresponding adjustments of the sliding cups with various tools and various apparatus is superfluous. For a sliding cup destined for a 28-mm ball-joint, the number of sizes of rings required, in which the sliding cup may be embedded, is limited to six and for a 32-mm ball-joint it is limited to three.

A further advantageous refinement of the invention is a tool for manipulation of the sliding cup provided with ring. With this, emplacement of a sliding cup into, and withdrawal from, the socket shell is possible. The tool possesses two components axially mobile with respect to each other, with the first component providing the support sitting on the rim of the socket shell and the second component, providing the force and tension in relation to the manipulation of the sliding cup, being able to be positioned on the sliding cup. The pressing and pulling arrangement is so constructed that, for emplacement of the sliding cup in the shell, it can be positioned on the securing elements to exert, by appropriate manipulation pressure on the securing elements, which are aligned with the socket shell and thereby insert the sliding cup in the socket shell, with the securing elements being pressed into the corresponding recesses.

To make possible release of the cup from the socket shell, the pressing and pulling arrangement is so designed that it can grip the securing elements, and upward pressure can be exerted on the sliding cup by movement of both components of the tool to extract it from the socket shell. While the support arrangement is supported on the rim of the shell, the pressing and pulling arrangement pulls the securing elements out of the recesses in the socket shell. Due to its mode of operation, the tool is comparable with a take-off device from sheet supports, but with the difference that here support does not take place on a centrally arranged sheet with the object to be removed arranged around the point of support, but that the object to be removed is located within the structure from which it must be extracted.

The invention is illustrated by diagrams as follows:

FIG. 2 shows a meridian-section through the socket, corresponding to the section position in FIG. 1.

Figure 1:
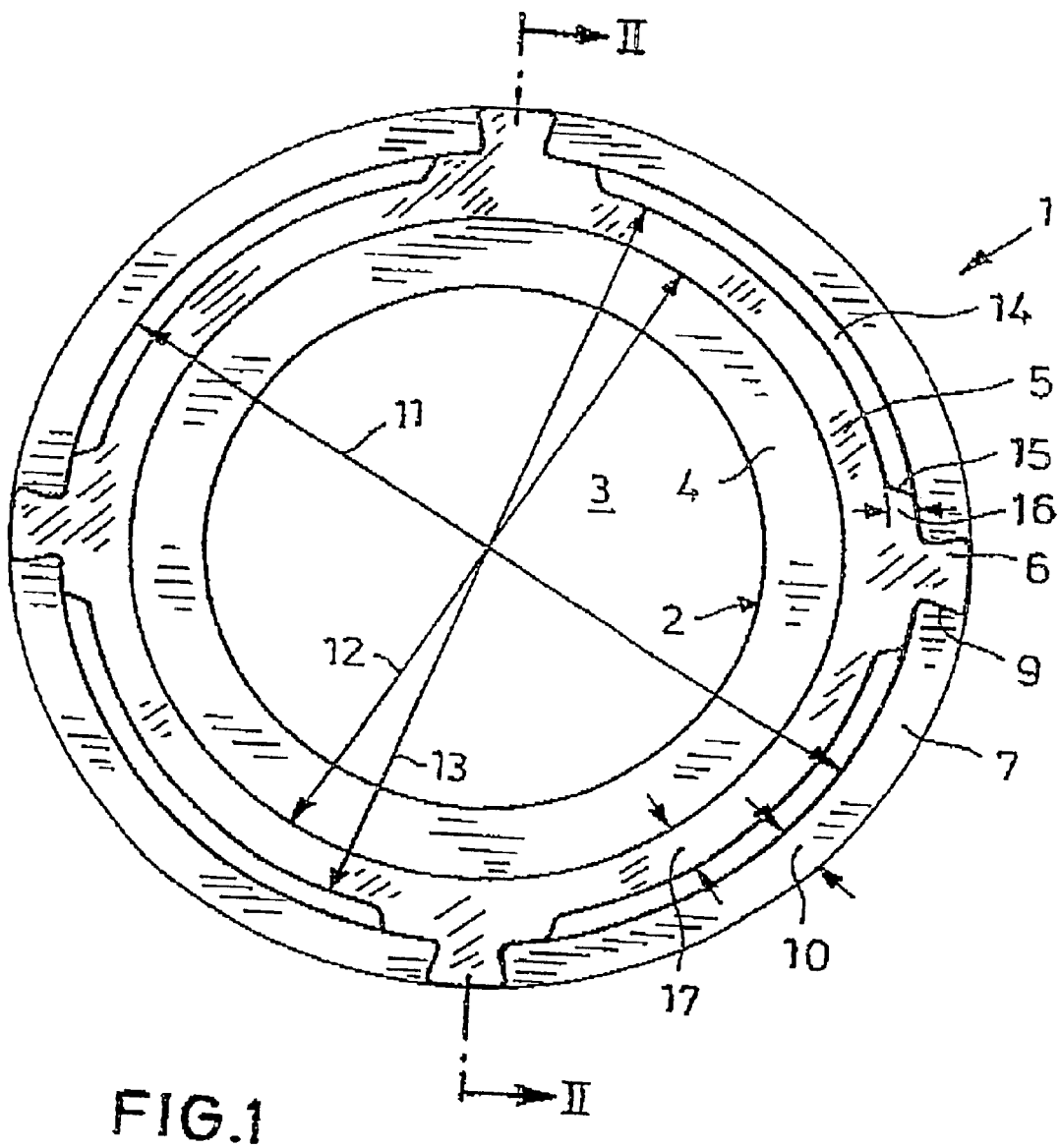
FIG. 1 shows a view of the modularly constructed socket according to the invention.
Figure 4:
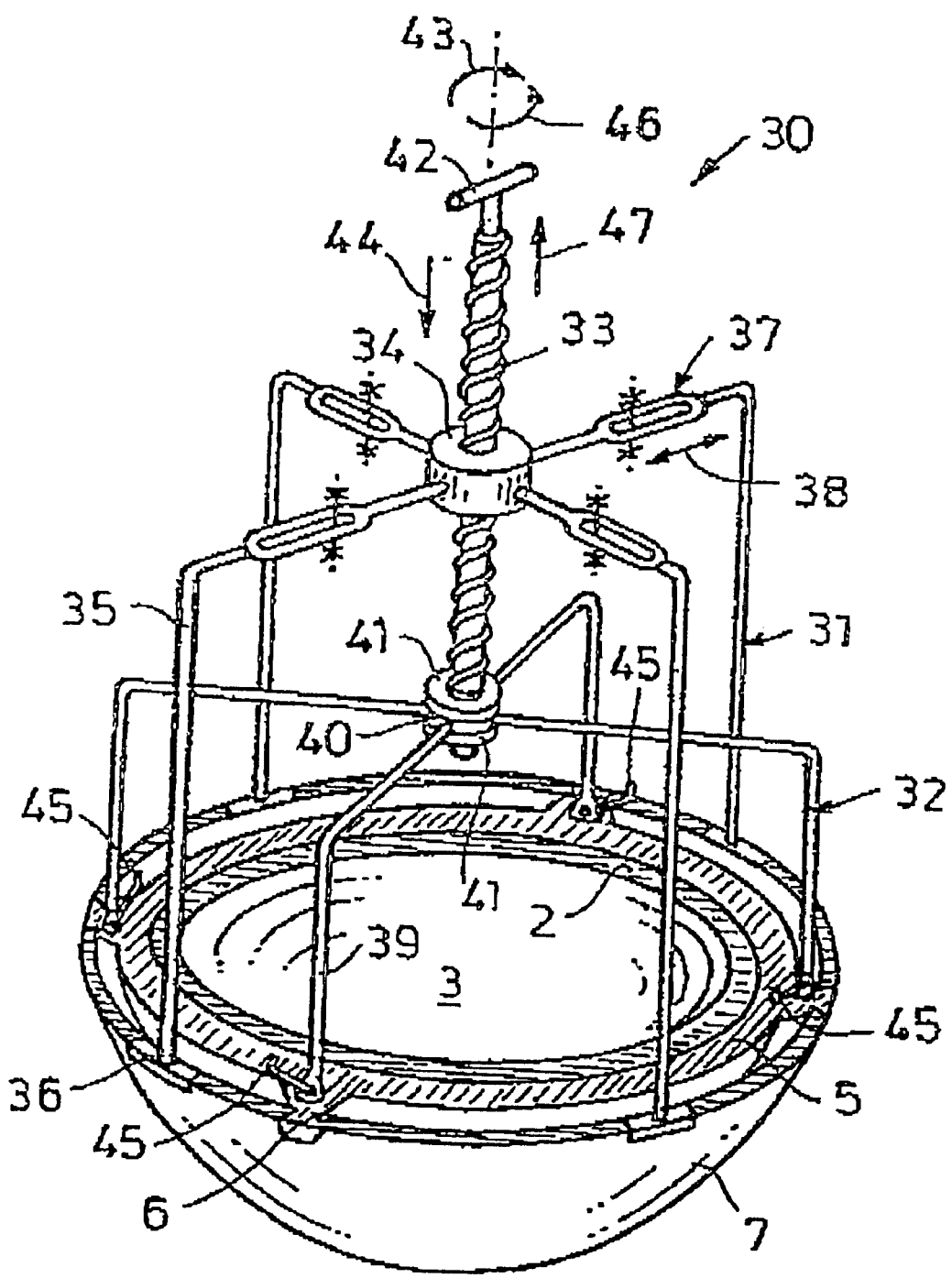

FIG. 3 shows detail of the section through a securing element in the wall of the socket housing and FIG. 4 shows a tool for manipulation of the sliding cup In FIG. 1 there is shown an enlarged view of a modularly constructed socket 1 of the invention. From the sliding cup 2 there is to be seen the sliding surface 3 and the front surface. The sliding cup 2 is surrounded by a ring 5 of biocompatible metal. The ring 5 in the present embodiment has four securing elements 6 distributed at regular intervals. The securing elements 6 are anchored in the socket shell 7. They engage there in correspondingly shaped recesses 8 (FIG. 3). The view of the securing elements 6 shows their wedge-shaped form 9 widening towards the outside. The socket shell 7 has a wall thickness 10 depending on its construction that can be between 2 mm and 5 mm. 11 is the internal diameter of socket shell 7 that accepts sliding cup 2. As can be seen, this internal diameter 11 is markedly larger than the external diameter 12 of sliding cup 2. It is also larger than the external diameter 13 of ring 5. Thus there is a gap 14 between ring 5 and socket shell 7. To ensure that the width of gap 14 is of uniform size, the securing elements 6 have so-termed spacers 15. The spacers 15, formed of the same material as the ring 5 and the securing elements 6, have a thickness 16, corresponding to the desired gap determined by the type of construction of the socket shell 7. The spacers 15 not only serve to ensure the uniform form of gap 14 but also ensure even support of ring 5 and thereby of the sliding cup 2 in the socket shell 7.

According to the invention, the external diameter 12 of a sliding cup 2 with a sliding surface 3 of assured diameter is constant for all types of structures of a shell 7. As a result of corresponding wall thickness 17 of ring 5, the difference between the internal diameter 11 of a socket shell 7 and the external diameter 12 of a sliding cup 2 is compensated for, so that the respective gap 14, which corresponds in width to the dimensions 16 of the spacer 15, is essentially of equal size in all types of shell structure. The gap 14 has a width 16, determined by the diameter of the sliding surface and the structure of socket shell 7, of between about 1 mm and about 1.8 mm. The wall thickness of wall 17 of the ring 5 thus ranges between about 2 mm and about 5 mm.

FIG. 2 shows a section though the modularly constructed socket 1 according to the invention corresponding to the section 11—11 depicted in FIG. 1. The section passes through two securing elements 6 opposite each other. As can be seen from FIG. 2, the ring 5 encloses the cup 2 at its external region 18 where, with conventional insertion of a sliding cup 2 in a socket shell, the clamping with the socket shell will take place. The connection between the ring 5 and the sliding cup 2 can be achieved comparably to the state-of-the-art conical clamp or by shrinking on. The height 19 of ring 5, just like with the conventional conical clamp in a shell, is about 10 mm. In order to avoid stresses at the transition positions between the sliding cup 2 and ring 5, in the clamping of the sliding cup 2, the ring tapers towards the sliding cup 2 in wedge shaped manner 21.

The present embodiment shows how the ring 5 with its spacers 15 lies on the shell 7. Furthermore, below the securing element 6 can be seen a notch 22 in which, not shown here, grippers of a tool can take hold, in order to lift the ring 5 with sliding cup 2 out of socket shell 7.

FIG. 3 shows the fit of a securing element 6 into the wall of socket 7. It is a cross-section, again enlarged. The securing element 6 has a trapezium-shaped cross-section 23. The recess 8 into which the securing element 6 fits has a cross-section 23 that matches the shape of securing element 6. The trapezium-shaped cross section 23 narrows in direction 24 of the forces acting on the cup 2 and the meridian of the shell 7 (FIG. 2), that, in the present embodiment, approximates to the shape of a spherical zone.

Because of the inclination of the actual sides 25 of the trapezium shaped securing elements 6 to the operating direction 2 of the forces, the force introduction into the socket shell 7 occurs with a component 26 in meridian direction 24 and with a component 27 perpendicular to it, corresponding to the latitudinal parallel. The sidewalls 25 are in the present embodiment, inclined at an angle 28 of about 15° relative to the meridians and the main direction of force 24.

In FIG. 4 a tool 30 is shown, with which a sliding cup 2 embedded in a ring may be fitted into a socket shell 7 or removed from it again. The depiction of tool 13 (sic) is purely diagrammatic and serves only to explain its mode of action.

Tool 30 has two components axially displaceable relative to each other, a support fitting 31 and a push-pull fitting 32, which are connected with each other by a threaded spindle 33, with the support fitting 31 being attached to a mother wheel nut 34 on the threaded spindle 33 and the push-pull fitting 32 itself being freely rotatable on the threaded spindle.

In the present embodiment, the support fitting 31 consists of four supports 35 parallel to each other and to the threaded spindle 33. The supports 35 have, as seen on the periphery of the wheel nut 34, equally sized angular separations. They rest with feet 36 on the rim of the shell 7. An adaptor fitting 37, not shown here in detail, allows the supports to be adapted to varying diameters of socket shell 7. Positioning can be effected for example by loosening the screws indicated here and by sliding the supports along the elongated holes corresponding to the double arrow 38.

The four supports 39 of the push-pull fitting 32 are determined in their number and arrangement by the securing elements 6 of ring 5. They are rigidly connected together with a ring 40 and arranged between the supports 35 of the support fitting 31. The ring may be freely drawn to the end of the threaded spindle 33 between two stop washers 41.

In the present embodiment, the mode of installing a sliding cup 2 in a socket shell 7 is presented. The supports 39 of the push-pull fitting 32 are placed on the securing elements 6. The supports 35 of the support fitting 31 rest on the rim of socket shell 7. By winding the handle 42 at the upper end of the threaded spindle 33 in the clockwise direction 43, the supports 39 of the push-pull fitting 32 move in the direction 44 and push the securing elements 6 into the recesses 8 of the socket shell 7. So that this pushing in can take place, pressure must also be exerted on the support fitting 31 in the direction of the arrow 44. The hooks 45 at the ends of support 39 used for removal of a sliding cup are raised up so that they do not hinder the insertion of sliding cup 2.

If the sliding cup 2 needs to be removed from socket shell 7, the hooks 45 at the end of supports 39 are fitted under the securing elements 6, so that they enter the notches 22. If then the threaded spindle 33 rotates in the anti-clockwise direction 46, while the support fitting 31 is supported on the rim of the socket shell 7, the push-pull fitting 32 moves in the direction of arrow 47 and thereby lifts the securing elements 6 out of the socket shell 7 and so removes the sliding cup 2 from socket shell 7.

What is claimed is:

1. Modularly constructed joint-socket for a ball-joint prosthesis to be inserted into bone tissue, consisting of a socket shell comprising an outer metal cup, inserted in the bone tissue, and an inner sliding cup of ceramic material slid into the socket shell, wherein the sliding cup is held fast by a ring made of biocompatible metal, that the ring has at least three securing elements extending outwardly radially, that the securing elements fit into recess in the socket shell and that the ring is separated from the socket shell by a gap.

2. Modularly constructed socket according to claim 1, wherein the sliding cup is held in the ring by a conical clamp.

3. Modularly constructed socket according to claim 1, wherein the ring is shrunk on to the sliding cup.

4. Modularly constructed socket according to claim 1, wherein the formation of a gap with constant distance between the sliding cup and the socket shell is achieved by spacers on the securing elements.

5. Modularly constructed socket according to claim 1, wherein the securing elements on the ring widen out in a radial direction in wedge-shaped manner and the recess in the socket shell match the contours of the securing elements.

6. Modularly constructed socket according to claim 1, wherein the securing elements narrow in a wedge shape in the direction of insertion into the socket shell and that the recesses in the socket shell match the contours of the securing elements.

7. Modularly constructed socket according to claim 1, wherein the external diameter of the sliding cup is constant and that, with varying internal diameter of the socket shell for accepting the sliding cup, the external diameter of the ring matches the internal diameter of the socket shell in such a way that the dimensions of the gap in the possible combinations of sliding cup and socket shell is always roughly the same.

8. Modularly constructed socket according to claim 1, wherein a tool for manipulation of the sliding cup fitted into a ring is provided to insert it into and extract it from the socket shell.

9. Modularly constructed socket according to claim 8, wherein the tool has two components axially displaceable relative to each other, that the first component is supported as support fitting by the rim of the socket shell and that the second component may be positioned as push-pull fitting on the securing elements of the sliding cup according to the intended manipulation of the sliding cup.

10. Modularly constructed socket according to claim 9, wherein insertion of the sliding cup in the socket shell, the push-pull fitting may be placed on the securing elements and the support fitting may be placed on the rim of the socket shell and that, by displacing the two components of the tool apart from each other on the sliding cup, a pressure is exerted in the direction of the socket shell.

11. Modularly socket according to claim 1, wherein for extraction of the sliding cup from the socket shell, the support fitting may be placed on the rim of the socket shell and the securing elements may be held by the push-pull fitting and that, by moving the two components of the apparatus closer together, the sliding cup can be extracted from the socket shell.

* * * * *